(12) United States Patent
Vodermayer et al.

(10) Patent No.: US 8,398,536 B2
(45) Date of Patent: Mar. 19, 2013

(54) IMPLANTABLE TWO-CHAMBER SYSTEM FOR SUPPORTING THE LEFT VENTRICLE OF THE HEART

(75) Inventors: Bernhard Vodermayer, Gilching (DE); Thomas Schmid, Gilching (DE)

(73) Assignee: Deutsches Zentrum fuer Luft- und Raumfahrt e.V., Cologne (DE)

( * ) Notice: Subject to any disclaimer, the term of this patent is extended or adjusted under 35 U.S.C. 154(b) by 419 days.

(21) Appl. No.: 12/309,663

(22) PCT Filed: Jul. 17, 2007

(86) PCT No.: PCT/EP2007/006314
§ 371 (c)(1), (2), (4) Date: Jan. 26, 2009

(87) PCT Pub. No.: WO2008/012007
PCT Pub. Date: Jan. 31, 2008

(65) Prior Publication Data
US 2009/0240097 A1 Sep. 24, 2009

(30) Foreign Application Priority Data
Jul. 28, 2006 (DE) .......................... 10 2006 035 798

(51) Int. Cl.
*A61N 1/362* (2006.01)
*A61N 1/00* (2006.01)
*A61B 5/02* (2006.01)
*A61M 5/178* (2006.01)

(52) U.S. Cl. .......... 600/16; 600/485; 607/3; 604/164.04

(58) Field of Classification Search .................... 600/16, 600/485; 607/3; 604/164.04
See application file for complete search history.

(56) References Cited

U.S. PATENT DOCUMENTS

| 5,314,469 A | 5/1994 | Gao |
| 6,949,065 B2 * | 9/2005 | Sporer et al. ................... 600/16 |
| 2002/0165426 A1 * | 11/2002 | Sporer et al. ................... 600/16 |

FOREIGN PATENT DOCUMENTS

| DE | 102 17 635 | 11/2002 |
| EP | 0 272 445 | 6/1988 |
| WO | WO 93/17730 | 9/1993 |

OTHER PUBLICATIONS

International Search Report.

* cited by examiner

*Primary Examiner* — Nicole F Lavert
(74) *Attorney, Agent, or Firm* — Collard & Roe, P.C.

(57) ABSTRACT

An implantable two-chamber system is for supporting the left ventricle of the heart. Each of the two pumping chambers (1, 1') of the two-chamber system is ventricular shaped including an inlet (11) and an outlet (12). A pressure plate (2) is rotatably mounted externally in two arms (5) which are movably retained on the output shaft (9) of a drive unit (15) such that the center of motion (8) of the arms (5), which lies on the output shaft (9), is located on the side of the pumping chamber (1, 1') facing away from adapters (4, 4'), and thus outside the pumping chambers (1, 1'). Each of the ventricular pumping chambers (1, 1') is provided with a bulge (13) in order to reduce the resistance to fluid flow, this bulge (13) having a length ranging from 10 to 15 percent of the length of the pumping chamber.

16 Claims, 3 Drawing Sheets

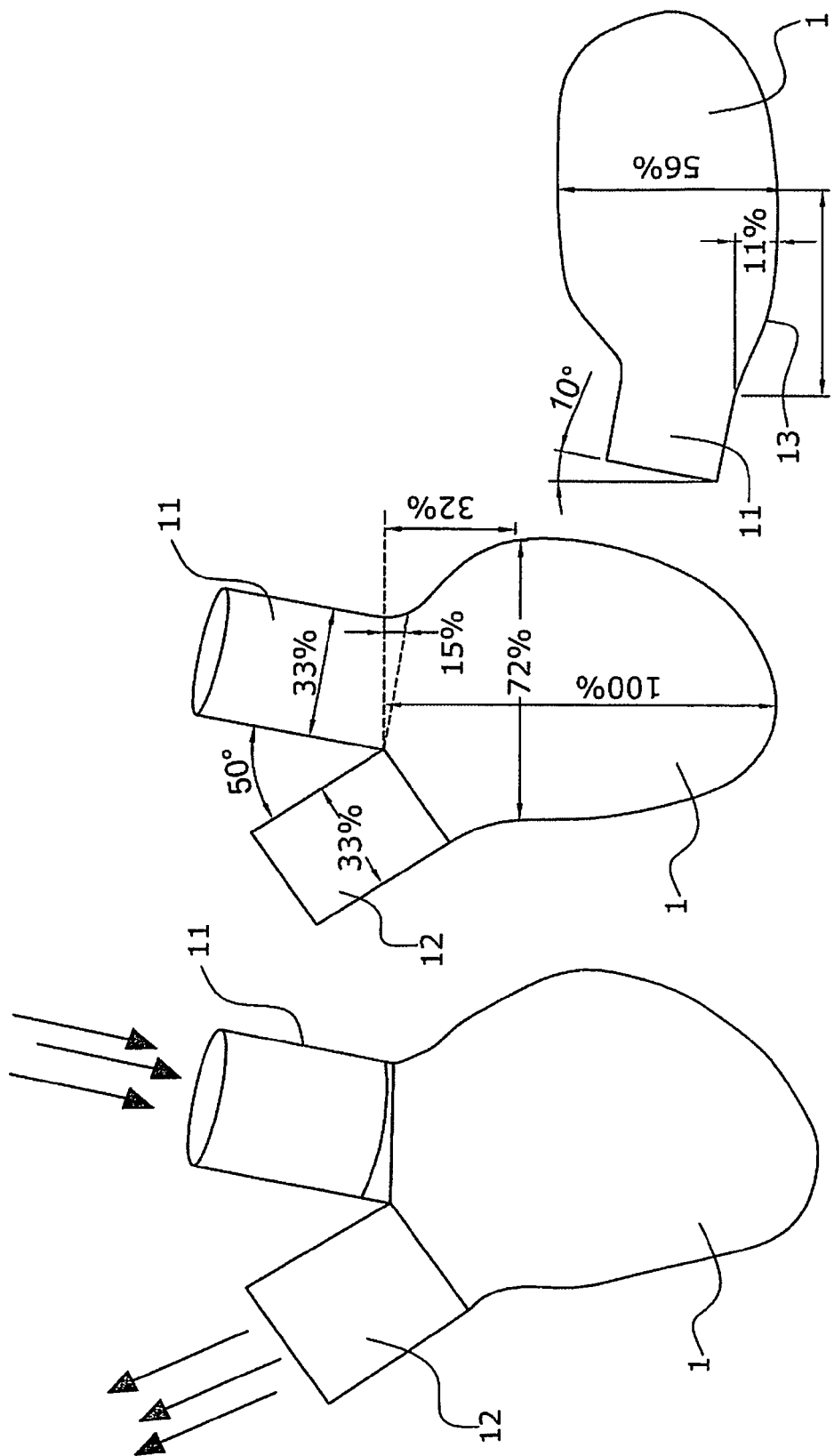

IMPLANTABLE TWO-CHAMBER SYSTEM FOR SUPPORTING THE LEFT VENTRICLE OF THE HEART

CROSS REFERENCE TO RELATED APPLICATIONS

This application is the National Stage of PCT/EP2007/006314 filed on Jul. 17, 2007, which claims priority under 35 U.S.C. §119 of German Application No. 10 2006 035 798.1 filed on Jul. 28, 2006. The international application under PCT article 21(2) was not published in English.

TECHNICAL FIELD

The invention relates to an implantable two-chamber system for supporting the left ventricle of the heart, comprising a pumping device formed by two pumping chambers and a pressure plate situated therebetween, which pressure plate is reciprocated between two end positions by a drive unit, whereby fluid is compressed in one pumping chamber, whereas the other is emptied.

Such a two-chamber system is described, for example, in DE 102 17 635 A1.

Mechanical circulation support systems (VAD: Ventricular Assist Device) are in clinical use since about 10 years and are the last option for saving a life in the event of a manifested cardiac insufficiency. Ventricular assist devices perform a part of the pumping work and thereby stabilize the circulation, until a donor organ is available. Recent studies show that, with this therapy, the cardiac function can improve so far that an explantation of the system is possible without a subsequent heart transplantation.

Artificial heart pumps are adaptable to various requirements and are available in clinics without any delay; however, they also have drawbacks and risks. In particular, the therapy is limited with respect to the technology implemented and the tolerability. Blood may be damaged by the pumping work. Supplying the necessary energy to the systems, which are presently operated exclusively electrically, via the abdominal wall bears a high risk of infection for the patient. Low efficiencies require high energy consumption and thereby the surrounding tissue is warmed. Assisted circulation must often be maintained for months or years. Such system are subject to high mechanical loads. Since it is not possible to change the blood pumps quickly, these have to be very robust and safe.

Since assist systems are implanted and are furthermore subject to great mechanical stresses, they have to be reliable and as physically compatible as possible. Problems mainly occur upon continuous stress and accompanying material fatigue, as well as with cardiac valves. Mechanical failure of the prostheses causes reduced pumping capacity. An unfavourable position leads to the formation of thromboses, preferably at the edge of the valves, and thereby reduces the effective opening diameter of the prosthesis. The number of the mobile parts, such as bearings, shafts, cams etc., presents an inherent risk; the lower this risk, the lower is the probability of failure of the overall system.

Ventricular assist devices, operating according to the principle of displacement, mechanically or pneumatically compress the pumping chamber, which requires an equalization of the displaced volume. Single-chamber systems have to compensate the compressed pumping volume via cannulas to the skin surface or via implanted volume equalization containers (so-called vents), which constitutes an additional risk. Single-chamber systems can also be used only to support one ventricle.

The formation of thromboses remains the major problem with the use of artificial blood pumps. A direct connection is assumed between the flow in the pumping chambers, the shearing forces caused thereby and the formation of clots. Depositions preferably occur in recirculation regions and when a separated flow is applied again. The destruction of red blood cells (haemolysis), however, could be proved in regions showing great shearing forces.

Previously implemented arc-shaped pumping chambers allow for a compact design, however, they cause recirculation and stagnation of the flow, whereby the formation of thromboses is facilitated. Regions of pronounced turbulences, as they are observed in the mostly round chambers of known systems, further reduce the efficiency of the pumps. Compression by means of a rigid pressure membrane strongly impedes the flow in the pumping chambers and propagates the formation of recirculation regions and depositions. Moreover, there is a risk of high shearing forces occurring at places where the flow is unfavourable, whereby the blood may be damaged.

SUMMARY OF THE INVENTION

Therefore, it is an object of the present invention to dimension and configure the pumping chambers of an implantable two-chamber system such that the fluid flow in the pumping chambers is as physiological a flow as possible, similar to the human heart. According to the invention, the object is achieved for an implantable two-chamber system according to the preamble of claim 1 with the features of the characterizing part thereof. Advantageous embodiments are the subject matter of claims referred directly or indirectly to claim 1.

According to the invention, each of both pumping chambers of the two-chamber system has the shape of a ventricular bag with an inlet formed under an acute angle with the outlet and immediately next to the same. Further, the pressure plate is rotatably mounted externally in two arms movably retained on the output shaft of a drive unit, so that the centre of motion of the arms, which lies on the output shaft, is located on the side of the pumping chambers averted from adapters and is thus located outside the pumping chambers.

Preferably, the angle between the inlet and outlet of each pumping chamber is between 30° and 60°. Further, the maximum width in the inlet and outlet region of each pumping chamber is approximately 65 to 72% of the respective pumping chamber length. The rest of the pumping chambers is of narrower configuration. Moreover, according to an advantageous embodiment, of the invention, each of the ventricle-shaped pumping chambers comprises a bulge of a length in the order of 10 to 15% of the pumping chamber length, the bulge being provided contiguous with the inlet to reduce the flow resistance. Furthermore, according to the invention, the inlet of each pumping chamber is inclined by about 10° with respect to the so-called pumping chamber bottom. To influence the flow velocity as little as possible both in the area of the inlet and in the area of the outlet, the diameter of the inlet and the outlet is about one third of the pumping chamber length.

According to the invention, both pumping chambers are optimized such that incoming fluid is impeded to a minimal extent, whereby an optimum flow profile can be formed in the chamber. Pumping chambers designed according to the invention, may thus be used not only in a two-chamber ventricular assist device, but also in single-chamber pumps.

In the pumping chambers configured according to the invention, it Is provided to use a rigid pressure plate, acting as a pressure membrane, which is profiled and rounded at the edge portion. The pumping chambers are also useful in connection with hydraulically or pneumatically operated pumps. When pumping chambers configured according to the invention are used, the energy consumption of the pump used can be reduced which is advantageous and desirably especially with implanted two-chamber systems.

According to an embodiment of the invention, the greatest thickness of the profiled pressure plate in the central region is about 10% of the pumping chamber length. The length of the pressure plate rounded at the edges is about 73%, whereas the largest width is about 66% of the pumping chamber length. To allow a bead to form at the edges of the pumping chambers, the overall width of the pressure plate may be narrower than the respective pumping chamber at maximum compression.

The use of a pressure plate, profiled and rounded at the edges as described above, in connection with the bulge formed at the ventricle-shaped pumping chambers, allows to obtain a moderate and uniform transition by directing an initially parallel flow from an adapter downward, the flow not separating from the wall. Thus, no losses due to a recirculation of the flow are caused.

Further, the bulge on the inlet side, in connection with the profiled pressure plate, increases the cross-sectional area between the pressure plate and the pumping chamber wall and thereby the flow resistance is substantially lower also at this site. This measure thus advantageously contributes to the formation of the above described favourable flow profile.

DESCRIPTION OF THE DRAWINGS

The following is a detailed description of the invention with reference to the drawings. In the Figures:

FIGS. 1a to 1c are a top plan view, a sectional view and a side elevational view of a pumping chamber in the form of a ventricle-shaped bag;

DESCRIPTION OF THE INVENTION

FIG. 1a and FIG. 1b are a top plan view and a sectional view of a pumping chamber 1 with an inlet 11 and an outlet 12. Here, the opening angle between the inlet 11 situated immediately near the outlet 12 and the outlet is in the range of about 30 to 60°. In FIG. 1b, the opening angle is illustrated in 50°.

Both the inlet 11 and the outlet 12 have comparatively large cross sections, whose diameter is about 33% of the length of the pumping chamber 1 indicated as 100% in FIG. 1b. The maximum width, below about the upper third in FIG. 1b (32% of the total chamber length), is about 72%. The adjacent portion of about two thirds of the total length of the pumping chamber is of narrower design.

As can be seen in the sectional view in FIG. 1c, the inlet 11 is inclined by about 10° in the so-called lateral plane. As is further obvious from FIG. 1c, the pumping chamber 1 has a bulge 13 at the "bottom", having a length in the order of 11% of the pumping chamber length. This bulge 13 with its large radius is provided to enlarge the cross section and to thereby reduce the flow velocity and the flow resistance.

Figures 2A, 2B, 2C:
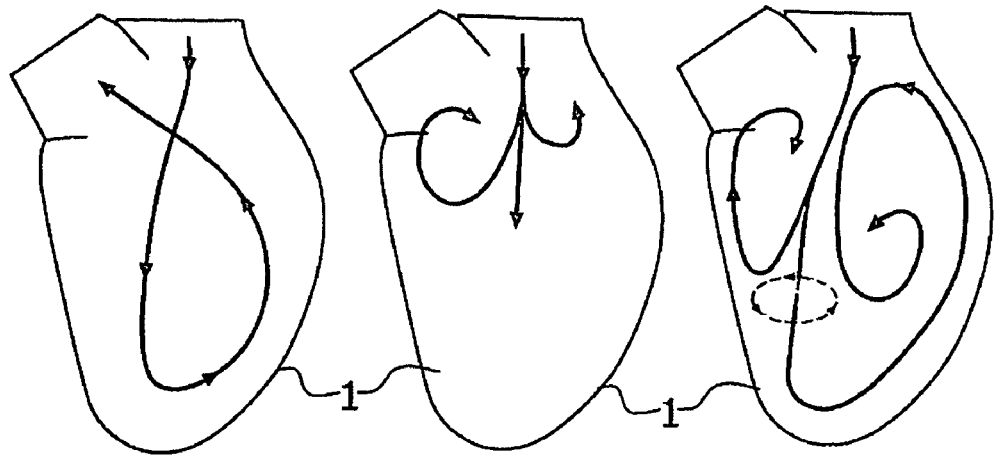
FIGS. 2a to 2c are schematic illustrations of different phases of a flow through a ventricle-shaped pumping chamber.

As indicated in FIG. 2b, due to the above described configuration of the pumping chamber 1, the flow is determined by a pronounced counter-clockwise turbulence as it forms because of the given geometry. In general, as indicated in FIG. 2a, the flow in the pumping chamber describes a kind of "8" whose upper circle is open. Here, in the systole, i.e. the compression phase, fluid flown in crosses the trajectory during the filling phase before the fluid is ejected. The deformation of the pumping chamber 1, still existing at the beginning of a filling phase, directs the inflowing fluid to the exterior chamber wall, as illustrated on the left in FIG. 2c. However, the counter-clockwise turbulence on the right in FIG. 2b dominates the chamber flow so that, as is clear from FIG. 2c, all portions of the pumping chamber 1 are optimally flown through. A chain-dotted ellipse with arrows, shown in the lower part of the pumping chamber 1, again highlights the above mentioned counter-clockwise turbulence.

Figure 3A:
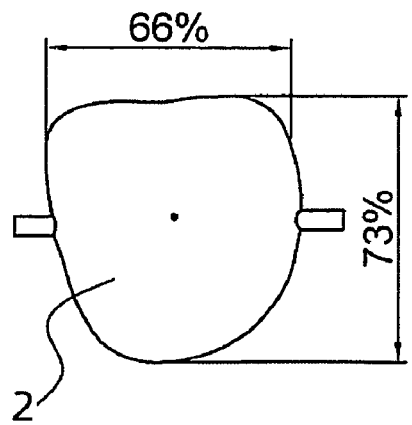
FIG. 3a is a top plan view on a pressure plate.
Figure 3B:
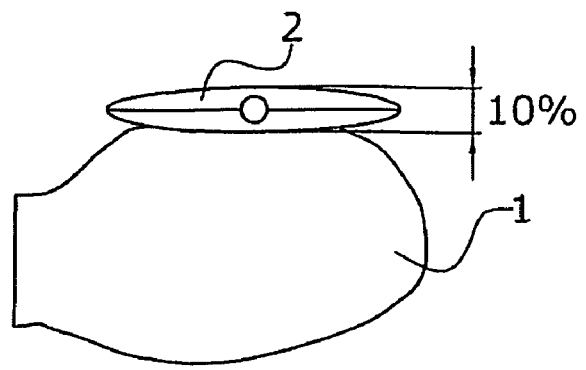
FIG. 3b is a side elevational view of the pressure plate lying on a pumping chamber.

As already mentioned, the pressure plate 2 is of a profiled design and has its edges rounded for an optimization of the flow. With a largest thickness at the centre being about 10 to 15% of the pumping chamber length, the length of the pressure plate 2, as can be seen in the illustration in FIG. 3a, is about 73% of the length of the pumping chamber; the largest width of the pressure plate is about 66% with respect to the length of the pumping chamber.

The pressure plate 2 may be narrower than the pumping chamber at maximum compression. In this manner, as also mentioned before, a bead can form at the edges and the flexible wall material of the pumping chamber 1 can deflect.

Figure 4:
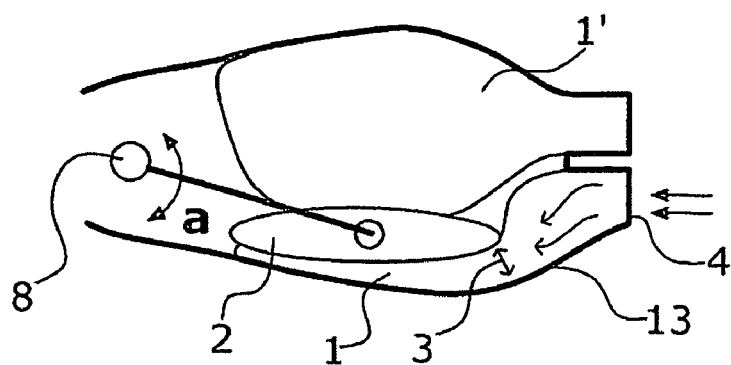
FIG. 4 is a sectional view of pumping chambers in a housing.

Because of the profiled pressure plate 2 and the above described bulge 13, a distinctly moderate and uniform transition is established in FIG. 4. The initially parallel flow, indicated by two horizontal arrows, from a schematically indicated feed adapter 4 is directed downward in FIG. 4 under an angle indicated by wavy lines with arrowheads, such that the fluid does not separate from the wall. Thus, no losses by a recirculation of the flow are caused either. As already detailed above, the bulge 13, as well as the profiled pressure plate 2 increase the cross-sectional area identified by the reference numeral 3, whereby the flow resistance is substantially reduced at this location, so that, overall, a favourable flow profile is achieved.

FIG. 4 approximately illustrates the moment when the fluid compression by the pressure plate 2 is finished and the filling phase of the pumping chamber 1, indicated by the lines with arrowheads, has just begun.

For example, in the initially mentioned DE 102 17 635 A, arms lie within the pressure plate, via which arms a drive unit drives and moves a pressure plate provided in the document; however, this is disadvantageous, since the arms repeatedly contact the pumping chamber walls and may possibly damage the same.

Figure 5:
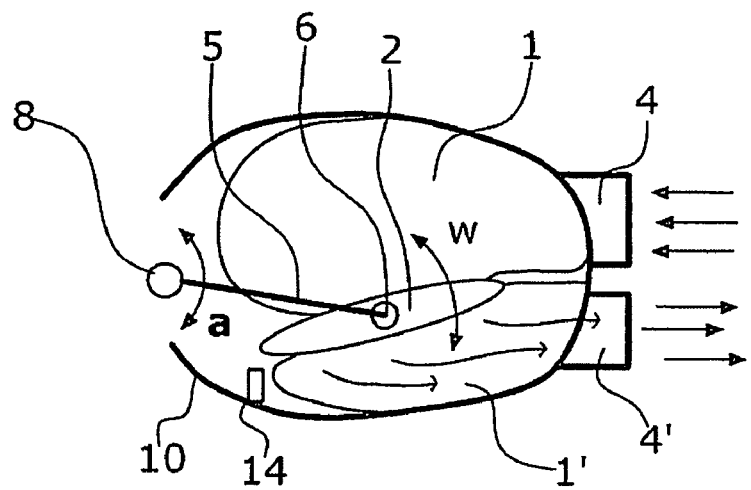
FIG. 5 is another sectional view of a housing with two pumping chambers.
Figure 6:
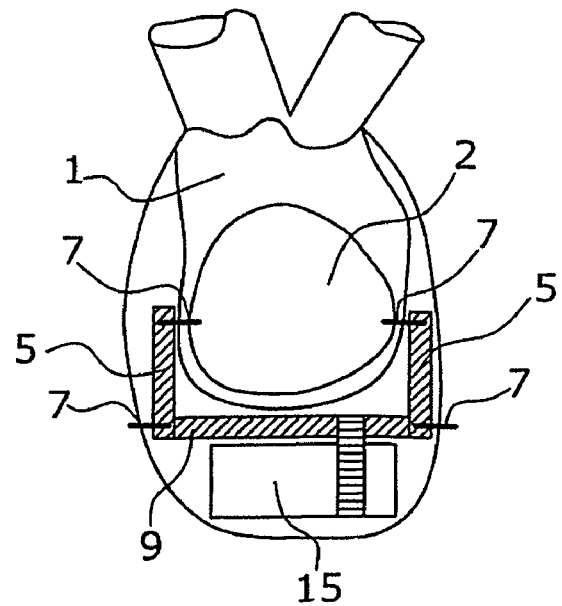
FIG. 6 is a schematic illustration of the guiding and supporting of the pressure plate relative to a pumping chamber.

To avoid this, the invention provides, as can be seen in the schematic illustration in FIG. 6, arms 5 arranged outside the pressure plate 2 and pivotably connected with the same via bearings 6 (FIG. 5) or pins 7 (FIG. 6). A centre of motion 8 of the arms 5, lying on the output shaft 9 of a drive unit 15 only schematically shown, is located on the side of the pumping chambers 1 and 1' averted from the adapters 4 and 4' and thus outside these pumping chambers.

By a pivoting movement of the arms 5 about the centre of motion 8 (following an arc a provided with arrowheads, FIG. 5), a corresponding pressure is exerted by the pressure plate 2 on the walls of the pumping chambers 1 and 1' and thereby on the fluid present in these chambers. The pivotably supported pressure plate 2 makes a kneading motion, as indicated in FIG. 5 by an arc w with arrowheads. This kneading motion additionally presses the fluid towards the adapter 4' (outlet) during the compression phase, as indicated by wavy arrow lines in FIG. 5.

A tilting of the pressure plate 2 to one side, as observed upon a lateral engagement and unfavourable pressure conditions, is thus not only avoided, but a substantially improved ejection of the fluid is achieved.

To even increase the kneading motion towards the end of a compression phase, an end stop 14 may be provided in an indicated housing 10 at the outer edge portion of the pivotably supported pressure plate 2, respectively. At the same time, the end stop 14 prevents the walls of the pumping chamber 1, 1' to contact each other when the arms 5 are deflected. Both pumping chambers 1, 1' are arranged such that only when the one pumping chamber is completely relieved, will the fluid in the other pumping chamber be compressed.

| List of reference numerals | |
|---|---|
| 1, 1' | pumping chamber |
| 2 | pressure plate |
| 3 | cross-sectional area |
| 4, 4' | adapter |
| 5 | arms |
| 6 | bearing |
| 7 | pin |
| 8 | centre of motion |
| 9 | output shaft |
| 10 | housing |
| 11 | inlet |
| 12 | outlet |
| 13 | bulge |
| 14 | end stop |
| 15 | drive unit |

The invention claimed is:

1. An implantable two-chamber system for supporting the left ventricle of the heart, comprising a pumping device and a drive unit, the pumping device comprising a first pumping chamber, a second pumping chamber, and a pressure plate arranged therebetween, the drive unit being able to reciprocate the pressure plate between two end positions,
   wherein fluid is compressed in the first pumping chamber at the same time that the second pumping chamber is emptied,
   wherein each of the first and second pumping chambers has:
      a shape of a ventricular bag,
      a first end,
      a second end,
      a pumping chamber length defined by the first end and the second end,
      an inlet formed at the first end and having a constant inlet diameter, and
      an outlet formed at the first end and having a constant outlet diameter,
   wherein the inlet is immediately beside the outlet such that at least an inner wall of the inlet meets an inner wall of the outlet,
   wherein the inlet is under an acute angle with the outlet, and
   wherein each of the first and second pumping chambers has a respective bulge for reducing flow resistance, the bulge being contiguous with the inlet and having a bulge length, the bulge length being 10 to 15% of the pumping chamber length.

2. The two-chamber system of claim 1, wherein the acute angle between the inlet and the outlet of each of the first and second pumping chambers is between 30° and 60°.

3. The two-chamber system of claim 1, wherein a first maximum width in an inlet region and a second maximum width in an outlet region of each of the first and second pumping chambers are about 65 to 72% of the respective pumping chamber length, and wherein the first and second pumping chambers are narrower in a region adjacent at least one of the inlet region and the outlet region.

4. The two-chamber system of claim 1, wherein the inlet of each of the first and second pumping chambers is inclined by about 10° to a pumping chamber bottom.

5. The two-chamber system of claim 1, wherein at least one of the constant inlet diameter and the constant outlet diameter is about one third of the pumping chamber length.

6. The two-chamber system of claim 5, wherein the pressure plate is profiled and rounded at an edge portion.

7. The two-chamber system of claim 1, wherein the two-chamber system further comprises adapters on a first side of the two-chamber system,
   wherein the drive unit is located outside of the first and second pumping chambers on a second side of the two chamber system, the second side being averted from the first side,
   wherein the drive unit comprises an output shaft and two arms movably retained at the output shaft,
   wherein the pressure plate is rotatably supported externally in the two arms, and
   wherein a center of motion of the two arms lies on the output shaft.

8. The two-chamber system of claim 7, wherein the pressure plate is slightly narrower than at least one of the first and second pumping chambers in a compressed state.

9. The two-chamber system of claim 7, wherein the pressure plate is less rigid in an outer portion than in a central portion.

10. The two-chamber system of claim 7, wherein the pressure plate is pivotably mounted in the two arms, and
    wherein, within a housing surrounding the first and second pumping chambers, a respective end stop is provided in an outer edge portion of the pressure plate.

11. The two-chamber system of claim 7, wherein a maximum thickness of the pressure plate in a central portion is about 5 to 15% of the pumping chamber length and a width and a length of the pressure plate amount to about two thirds of the pumping chamber length.

12. The two-chamber system of claim 8, wherein a maximum thickness of the pressure plate in a central portion is about 5 to 15% of the pumping chamber length and a width and a length of the pressure plate amount to about two thirds of the pumping chamber length.

13. The two-chamber system of claim 6, wherein a maximum thickness of the pressure plate in a central portion is about 5 to 15% of the pumping chamber length and a width and a length of the pressure plate amount to about two thirds of the pumping chamber length.

14. The two-chamber system of claim 8, wherein the pressure plate is less rigid in an outer portion than in a central portion.

15. The two-chamber system of claim 6, wherein the pressure plate is less rigid in an outer portion than in a central portion.

16. The two-chamber system of claim 11, wherein the pressure plate is less rigid in an outer portion than in the central portion.

* * * * *